US009243221B2

(12) United States Patent
Yarmush et al.

(10) Patent No.: US 9,243,221 B2
(45) Date of Patent: Jan. 26, 2016

(54) COMPOSITIONS AND METHODS OF FUNCTIONALLY ENHANCED IN VITRO CELL CULTURE SYSTEM

(75) Inventors: Martin Yarmush, Newton, MA (US); Robert Freedman, Beverly Hills, CA (US); Yaakov Nahmias, Plymouth, MN (US); Eric Novik, Edison, NJ (US)

(73) Assignees: HUREL CORPORATION, Beverly Hills, CA (US); THE GENERAL HOSPITAL CORPORATION, Boston, MA (US)

( * ) Notice: Subject to any disclaimer, the term of this patent is extended or adjusted under 35 U.S.C. 154(b) by 496 days.

(21) Appl. No.: 13/131,041

(22) PCT Filed: Nov. 24, 2009

(86) PCT No.: PCT/US2009/065781
§ 371 (c)(1),
(2), (4) Date: Feb. 2, 2012

(87) PCT Pub. No.: WO2010/062911
PCT Pub. Date: Jun. 3, 2010

(65) Prior Publication Data
US 2012/0129207 A1    May 24, 2012

Related U.S. Application Data

(60) Provisional application No. 61/118,362, filed on Nov. 26, 2008.

(51) Int. Cl.
*C12N 5/071* (2010.01)
*C12Q 1/02* (2006.01)
*C12M 1/42* (2006.01)
*C12M 1/32* (2006.01)
*C12M 3/06* (2006.01)
*C12M 1/12* (2006.01)

(52) U.S. Cl.
CPC .............. *C12M 35/08* (2013.01); *C12M 23/12* (2013.01); *C12M 23/16* (2013.01); *C12M 25/14* (2013.01)

(58) Field of Classification Search
None
See application file for complete search history.

(56) References Cited

U.S. PATENT DOCUMENTS

| 2005/0032205 A1 | 2/2005 | Smith et al. | |
| 2005/0266393 A1* | 12/2005 | Baxter et al. | 435/4 |
| 2007/0224677 A1 | 9/2007 | Neumann | |
| 2007/0275882 A1 | 11/2007 | Meijer et al. | |
| 2008/0009027 A1* | 1/2008 | Fraker et al. | 435/29 |

FOREIGN PATENT DOCUMENTS

| EP | 1548031 A1 | 6/2005 |
| WO | WO 2005063809 A1 * | 7/2005 |

OTHER PUBLICATIONS

Schiff et al., Organ Culture of Adult Rat Colonic Mucosa on Fibrin Foam, In Vitro, 1980, vol. 16, pp. 893-906.*
Hung et al., Continuous Perfusion Microfluidic Cell Culture Array for High-Throughput Cell-Based Assays, Biotechnology and Bioengineering , 2004, vol. 89, pp. 1-8.*
Nahmias et al., A novel formulation of oxygen-carrying matrix enhances liver-specific function of cultured hepatocytes, The FASEB Journal, 2006, vol. 20, pp. E1828-E1836.*
Evdokimova et al., Effects of bacterial endotoxin (lipopolysaccharides) on survival and metabolism of cultured precision-cut rat liver slices, Toxicology in Vitro, 2002, vol. 16, pp. 47-54.*
Krause et al., Hepatocytmupported serum-free culture of rat liver sinusoidal endothelial cells, Journal of Hepatology, 2000, vol. 32, pp. 718-726.*
Corning Inc., Life Sciences, Reducing Serum Levels and Culture Costs, 2005, pp. 1-4.*
Van de Bovenkamp et al., Precision-cut fibrotic rat liver slices as a new model to test the effects of anti-fibrotic drugs in vitro, Journal of Hepatology, 2006, vol. 45, pp. 696-703.*
Van de Bovenkamp et al., Liver fibrosis in vitro: Cell culture models and precision-cut liver slices, Toxicology in Vitro, 2007, vol. 21, pp. 545-557.*
Boess et al., Gene Expression in Two Hepatic Cell Lines, Cultured Primary Hepatocytes, and Liver Slices Compared to the in Vivo Liver Gene Expression in Rats: Possible Implications for Toxicogenomics Use of in Vitro Systems, Toxicological Sciences, 2003, vol. 73, pp. 386-402.*
International Search Report for PCT/US2009/065781, mailed Jul. 30, 2010.
Written Opinion of the International Searching Authority for PCT/US2009/065781, mailed 30, 2010.
Kidambi, S. et al., "Oxygen-mediated enhancement of primary hepatocyte metabolism, functional polarization, gene expression, and drug clearance," PNAS, vol. 106, No. 37, pp. 15714-15719 (2009).
Rotem, A. et al., "Oxygen Is a Factor Determining In Vitro Tissue Assembly: Effects on Attachment and Spreading of Hepatocytes," Biotechnology and Bioengineering, vol. 43, pp. 654-660 (1994).

(Continued)

*Primary Examiner* — Louise W Humphrey
*Assistant Examiner* — Christopher Keller
(74) *Attorney, Agent, or Firm* — Law Office of Salvatore Arrigo and Scott Lee, LLP

(57) ABSTRACT

Compositions and methods described herein provide a cell culture system in which cells are in high metabolic states from the onset of the culture. Combinations of various cell culture components disclosed and employed herein allow cells to be in high metabolic states useful for drug testing immediately after the start of cell culture.

24 Claims, 8 Drawing Sheets

(56) References Cited

OTHER PUBLICATIONS

Suleiman S.A. et al., "The Effect of Oxygen Tension on Rat Hepatocytes in Short-Term Culture," In Vitro Cellular & Developmental Biology, vol. 23, No. 5, pp. 333-338 (1987).

Tilles, A. W., et al., "Effects of Oxygenation and Flow on the Viability and Function of Rat Hepatocytes Cocultured in a Microchannel Flat-Plate Bioreactor," Biotechnol Bioeng, vol. 73, pp. 379-389 (2001).

Yanagi, K. et al., "Improvement of Metabolic Performance of Cultured Hepatocytes by High Oxygen Tension in the Atmosphere," Artificial Organs, vol. 25, No. 1, pp. 1-6 (2001).

* cited by examiner

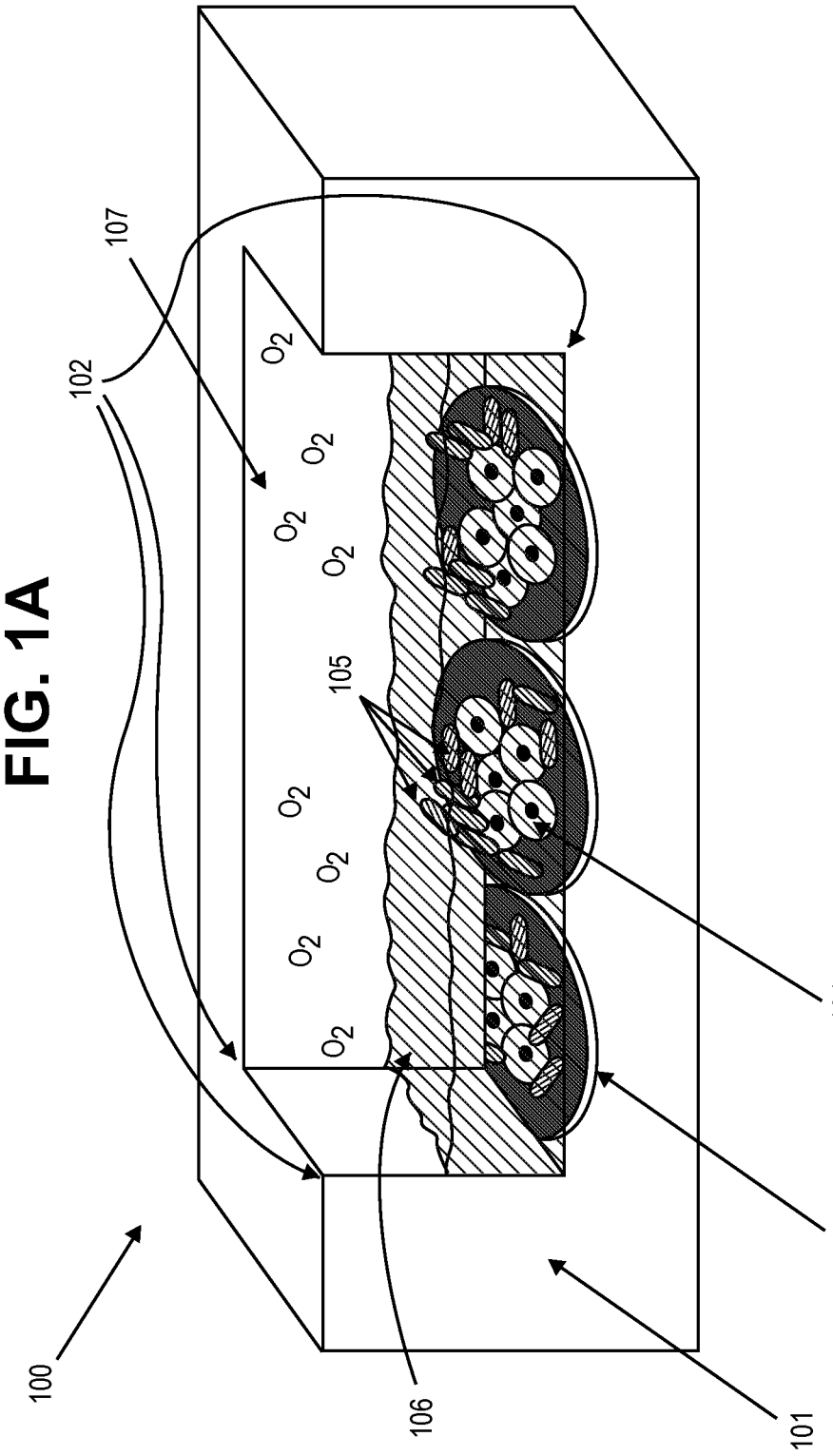

COMPOSITIONS AND METHODS OF FUNCTIONALLY ENHANCED IN VITRO CELL CULTURE SYSTEM

CROSS-REFERENCE

This application is the U.S. National Stage of International Application No. PCT/US2009/065781, filed Nov. 24, 2009, which claims the benefit of U.S. Provisional Application No. 61/118,362, filed Nov. 26, 2008, both of which are incorporated herein by reference.

GOVERNMENT SUPPORT

This invention was made with Government support under Grant Numbers EB002503 and DK080241 awarded by the National Institutes of Health. The Government has certain rights in this invention.

BACKGROUND OF THE INVENTION

The liver constitutes a central site in the absorption, binding, distribution, metabolism, excretion, and toxicogenicity (absorption, distribution, metabolism, excretion and toxicity, "ADME-T") of xenogenous materials (i.e. materials foreign to the body in their origination). When a xenobiotic entity, such as a drug, pharmaceutical, or nutriceutical, enters a human body, it is frequently cleared (i.e., metabolically disposed of) in the liver by oxidation, reduction, hydroloysis, and/or hydration steps of biochemical reaction. Of the over a dozen different cell types that comprise the liver, the hepatocyte is the type primarily responsible for playing the role of "clearing house" or "biotransformation driver," metabolically disposing of xenogenous material. In the liver, the hepatocyte is the cell type wherein a family of enzymes named cytochrome P-450 or CYP450 are chiefly expressed, along with other enzymes that also mediate the Phase I as well as the Phase II metabolic disposition of drugs, and other xenogenous materials. The various CYP450 isozymes collectively comprise the most important group of metabolizing enzymes that perform the role of clearing house. The field of study of how the body disposes of xenobiotic entities is frequently called Drug Metabolism and Pharmacokinetics, or DMPK. The term "pharmacokinetics" is often used in contradistinction to the term "pharmacodynamics." Pharmacodynamics signifies the impacts and effects that a drug may biochemically exert upon a cell, an organ or an entire animal; whereas pharmacokinetics signifies the impacts, effects and ultimate disposition that a cell, organ or entire animal may biochemically exert upon a xenogenous chemical entity. In everyday language, pharmacodynamics comprises what the drug does to the body, while pharmacokinetics comprises what the body does to the drug. Toxicity, including hepatotoxicity, is a major category of pharmacodynamic effect (drug efficacy being another such major category); while drug absorption, metabolism, distribution, and excretion comprise the major categories of pharmacokinetic effects.

In addition to metabolic function, signaling interactions constitute another important category of cellular function in the liver and in other organs. Classes of proteins called chemokines or cytokines, among others, frequently effectuate signaling interactions. Modern biotechnology has led to the delineation of a variety of molecular signaling pathways in the cell. These signaling pathways not only have provided insights into the mechanisms of a cell, but also have opened opportunities to intervene with cellular processes or abnormalities. Antibodies, vaccines and other forms of chemical entities have been utilized to specifically promote, inhibit, induce, or reduce one or more signaling pathways.

Many attributes of a molecular entity must be investigated and in some cases chemically modified or improved in the course of developing that molecular entity into a therapeutically efficacious and safe compound that regulatory agencies approve for marketing and clinical use. One challenge is investigating and if necessary overcoming any toxicity that the drug candidate may directly or indirectly induce. Another set of challenges is to understand and in some circumstances to improve the pharmacokinetic properties of the molecular entity. Studying and if possible improving the efficacy of the molecular entity to achieve an intended biochemical result comprises a third set of challenges to be addressed along the path of discovering, developing, testing, and ultimately receiving marketing approval for a new drug.

To address the kinds of challenges enumerated above, in vitro cell-based assay systems are frequently utilized to simulate, measure and/or predict various functional attributes (including without limitation those elaborated in the paragraphs above) of liver cells as well as of cells from other organs comprising a mammalian organism, and of the various organs themselves. These assays may be variously utilized for analytic, therapeutic, diagnostic, or industrial purposes. However, at the current state of the art, such in vitro cell-based assay systems possess limitations that impose high costs, or that limit the simulative or predictive capacities of the assay (which in turn imposes high costs when the simulative or predictive results of the assay are found to be of no or limited use). One form of limitation that currently, frequently occurs in in vitro cell-based assay systems is that the configuration of the system causes the degree of metabolic or other functional competency of the cultured cells to remain at too low a level to yield accurate, or measurable, results that afford a useful prediction of how a chemical entity being tested on the system will interact with a cell, an organ, an organ system or an entire organism in vivo. Another challenge of cell-based systems is that the system is configured such that a level of cellular functionality, once achieved, cannot be maintained over a desirable duration of time. Another such form of limitation is that the amount of time that must be devoted to the initial incubation and/or culture of the cellular materials, prior to the time when the cells assume the higher or highest degrees of functionality of which they become capable, is a time of long duration. Improvements to the state of the relevant art, which may serve to reduce any of these or other limitations or their impacts, will provide more accurate and cost-effective means of using cellular cultures.

SUMMARY OF THE INVENTION

Present herein is a system in which cells are maintained in a metabolically highly active state from close to the onset of the culture. The system may be utilized to test the potential toxicological impacts of constituent components of consumer and industrial products, to study the environmental impacts of pollutants and other chemicals, to detect the presence of chemical and bioweapons, to analyze the pharmacologic, pharmacokinetic and toxicological properties of molecular entities, and to study other interactions between cellular materials and chemical or molecular entities.

From a commercial standpoint, certain cell types are not useful if they exist in a low metabolic state. For example, testing drugs for hepatotoxicity frequently cannot be adequately accomplished if the hepatocytes are in a low metabolic state. Therefore, the period during which the cells are in a low metabolic state constitutes a period of low, no, or wasted productivity in economic terms.

Despite the absence or loss of productivity in the time during which the low metabolic state obtains which may be as long as a week or longer, such initial phase has been viewed and accepted by industrial and academic scientists as an unavoidable prerequisite that must be endured in order to reach at a later point of time a culture characterized by a higher metabolic or other functional state.

As presented herein there are embodiments in which the initial phase of low metabolic state is reduced significantly to an extent that useful applications of cultured cells are provided. In other aspects, other embodiments are described in which other limitations associated with traditional cell culture are reduced significantly to an extent that useful applications of cultured cells are provided.

Compositions and methods described herein utilize multiple cell culture components. Each of the components of the system plays a role distinct from the other components. Combinations of various cell culture components give rise to various embodiments of compositions and methods described herein. Also, each cell culture component may have one or more embodiments. These cell culture components combine together to provide unexpectedly rapidly arising and high level of metabolic or other cellular function of the cultured cells.

In one aspect, a cell culture component is a high oxygen environment during cell seeding.

In one aspect, a cell culture component is a high oxygen environment during cell culture.

In one aspect, a cell culture component is the absence of serum in the culture media. Alternatively, said cell culture component is a low level of serum in the culture media.

In one aspect, a cell culture component is the use of material that enables the cells to assume a three-dimensional ("3D") relationship to each other. In one embodiment, the cell culture component is a three-dimensional scaffold. Alternatively, said cell culture component is a gel sandwich, a gel overlay, a micropatterned array of cells, cells configured in a spheroid, a tissue segment, a tissue slice, or an artificial tissue construct.

In one aspect, a cell culture component is a cell cultured in the presence of at least one additional cell type.

In one aspect, a cell culture component is liquid or gaseous cell culture medium that is configured to contact cultured cellular materials including cells cultured in a mono-layer, cells cultured in a 3D relationship to each other, cells cultured in a co-culture, subcellular materials, subcellular components, and cellular products—under at least one condition of actuated perfusion or flow.

Compositions and methods described herein comprise a cell culture system comprising at least one compartment for culturing cells, a culture of a first population of metabolically active cells and at least two cell culture components selected from: (i) a cell culture environment with an oxygen concentration higher than the atmospheric concentration, (ii) a second cell population for co-culture with said first population of cells and/or a structure configured for three-dimensional culture of said first population of cells with or without a second cell population for co-culture with said first population of cells; (iii) a serum-free culture medium or culture medium with a low concentration of serum; and (iv) a cell culture medium that is configured to contact or come into proximity with said first population of cells under at least one condition of actuated perfusion or flow.

In one aspect of said cell culture system, said first population of cells comprises hepatocytes.

In one aspect of said cell culture system, said structure for three-dimensional culturing comprises a gel sandwich culture, a gel overlay culture, a micropatterned overlay culture, a scaffold, a tissue slice, a tissue segment culture, or an artificial tissue construct.

In one aspect of said cell culture system, said second cell population comprises non-parenchymal cells, stromal cells or immune cells.

In one aspect of said cell culture system, said cell culture environment comprises about 95% oxygen and about 5% $CO_2$.

In one aspect of said cell culture system, said culture medium is circulated to said at least one compartment under actuated flow or perfusion through at least one microfluidic channel.

In one aspect, said cell culture system comprise a cell culture environment comprising about 95% oxygen and about 5% $CO_2$, a three-dimensional culture comprising hepatocytes and fibroblasts and a serum-free culture media. In another aspect, said cell culture system further comprises a cell binding material on said compartment for attachment of said cells. In another aspect, said cell culture system further comprises at least one subcellular component contained in the at least one compartment or another separate compartment.

Compositions and methods described herein comprise a method of culturing a first population of metabolically active cells comprising culturing said cells in the presence of at least two cell culture components selected from: (i) a cell culture environment with an oxygen concentration higher than the atmospheric concentration, (ii) a second cell population for co-culture with said first population of cells and/or a structure configured for three-dimensional culture of said first population of cells with or without a second cell population for co-culture with said first population of cells; (iii) a serum-free culture medium or culture medium with a low concentration of serum; and (iv) a cell culture medium that is configured to contact or come into proximity with said first population of cells under at least one condition of actuated perfusion or flow.

In one aspect of said method of culturing, said first population of cells comprises hepatocytes. Alternatively, said first population comprises kidney cells or keratinocytes.

In one aspect of said method of culturing, said oxygen concentration is higher than atmospheric for the seeding of said first population of cells.

In one aspect of said method of culturing, said structure for three-dimensional culturing comprises a gel sandwich culture, a gel overlay culture, a micropatterned overlay culture, a scaffold, a tissue slice, a tissue segment culture, or an artificial tissue construct.

In one aspect of said method of culturing, said second cell population comprises fibroblasts, glial cells, endothelial cells, stromal cells or non-parenchymal cells.

In one aspect of said method of culturing, said cell culture environment comprises about 95% oxygen and about 5% $CO_2$.

In one aspect of said method of culturing, primary cell hepatocytes are seeded onto a three-dimensional cell culture structure together with secondary cells comprising fibroblasts in an environment comprising about 95% oxygen and about 5% $CO_2$ and cultured in a serum-free medium.

In one aspect of said method of culturing, said compartment further comprises a coating of a binding material for attachment of said cells.

Compositions and methods described herein comprise a method of screening a material for its pharmacologic, metabolic, pharmacokinetic, or toxicological properties comprising culturing a first population of metabolically active cells in the presence of at least two cell culture components selected from: (i) a cell culture environment with an oxygen concentration higher than the atmospheric concentration; (ii) a second cell population for co-culture with said first population of cells and/or a structure configured for three-dimensional culture of said first population of cells with or without a second cell population for co-culture with said first population of cells; (iii) a serum-free culture medium or culture medium with a low concentration of serum; and (iv) a cell culture medium that is configured to contact or come into proximity with said first population of cells under at least one condition of actuated perfusion or flow.

In one aspect of said method of screening, said method further comprises measuring an activity of said first population of cells.

In one aspect of said method of screening, said primary cells comprise hepatocytes. Alternatively, said primary cells comprise kidney cells or keratinocytes.

In one aspect of said method of screening, said activity of said first cells comprises a metabolite, a biomarker, gene expression, or protein activity.

In one aspect of said method of screening, said oxygen concentration is higher than atmospheric for the seeding of said primary cells.

In one aspect of said method of screening, said structure for three-dimensional culturing comprises a gel sandwich culture, a gel overlay culture, a micropatterned overlay culture, a scaffold, a tissue slice, a tissue segment culture, or an artificial tissue construct.

In one aspect of said method of screening, said method further comprises contacting said first cells or the cell culture media from said first cells with a subcellular component. In another aspect of said method of screening, said method further comprises measuring an activity of said subcellular component.

Compositions and methods described herein comprise a kit for culturing cells comprising: (i) a device for culturing cells containing at least one compartment, each compartment filled with serum-free cell culture medium; (ii) a vial of a first population of cryopreserved metabolically active cells; (iii) a vial of a second population of cryopreserved cells; and (iv) a canister of gases comprising about 95% oxygen and about 5% $CO_2$.

In one aspect of said kit, said first population of cells comprise hepatocytes.

In one aspect of said kit, said kit further comprises a scaffold for three-dimensional cell growth at least one compartment.

In one aspect of said kit, said device comprises a microtiter plate.

In one aspect of said kit, said device comprises a chip with at least one microfluidic channel adapted to flow culture media through said at least one compartment.

In one embodiment of compositions and methods described herein, the system comprises multiple cell culture components.

In one embodiment of compositions and methods described herein, the system employs three cell culture components.

In one embodiment of compositions and methods described herein, the system employs two cell culture components.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of compositions and methods described herein are set forth with particularity in the appended claims. A better understanding of the features and advantages of compositions and methods described herein will be obtained by reference to the following detailed description that sets forth illustrative embodiments, in which the principles of compositions and methods described herein are utilized, and the accompanying drawings of which:

FIGS. 1 and 1A illustrates an embodiment of compositions and methods described herein comprising multiple cell culture components.

DETAILED DESCRIPTION OF THE INVENTION

Figure 1:
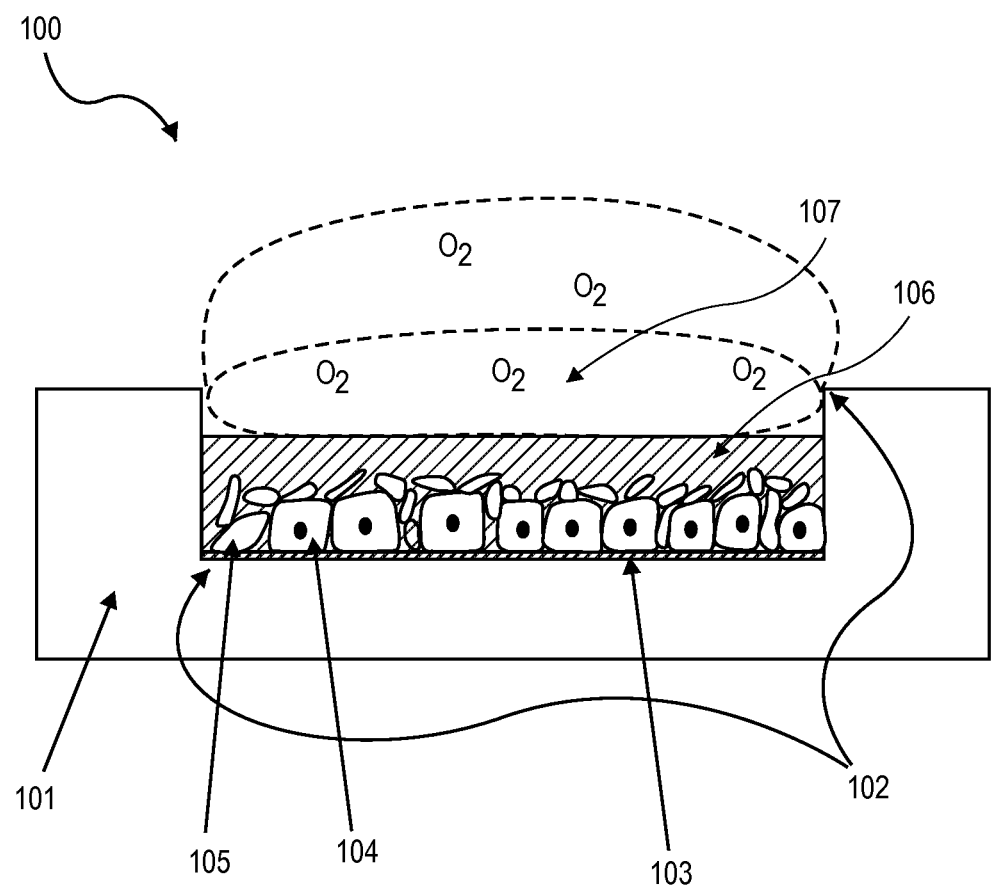

While preferred embodiments of compositions and methods described herein have been shown and described herein, it will be obvious to those skilled in the art that such embodiments are provided by way of example only. Numerous variations, changes, and substitutions will now occur to those skilled in the art without departing from compositions and methods described herein. It should be understood that various alternatives to the embodiments of compositions and methods described herein may be employed in practicing compositions and methods described herein. It is intended that the following claims define the scope of compositions and methods described herein and that methods and structures within the scope of these claims and that their equivalents be covered thereby.

Described herein are configurations of elements of a cell culture system for the purpose of producing, in an in vitro environment, the enhanced cellular functionality of the cells cultured therein, their subcellular components, cellular products, or cellular materials, to an extent determined either in terms of at least one of either (a) improved degree of superior functionality achieved or (b) the improved rapidity with which any particular degree of functionality is achieved than may be achievable by any alternative cell culture system that does not comprise the component elements that are configured in compositions and methods described herein. Enhanced cellular functionality may comprise the cell's enhanced ability to synthesize proteins or other cellular products; to maintain the functionality of organelles or other subcellular components, such as mitochondria; to produce cytokines; to express genes; or to transport or metabolize xenogenous materials with which the cell comes in contact; or to perform any other cellular function Enhanced cellular functionality may comprise the degree, or extent, to which the cell manifests any of the foregoing functions.

Presented herein is a cell culture system in which cells rapidly achieve and maintain a metabolically highly active state from close to the onset of the culture. Various combinations of the cell culture components described provide highly functional cells while diminishing the time required to achieve such high functionality, thus reducing time lost for productive use of the cultures.

From a commercial standpoint, certain cell types are not useful if they exist in a low metabolic state, i.e., at a low level of metabolic competency. For example, with respect to cultured hepatocytes, testing for the hepatotoxicity or clearance of chemical entities, or the generation of metabolites derived from such entities, is not effective if the hepatocytes exist in a low metabolic state. The period in which cells are in said low metabolic state thus constitutes a period of low, or no, or wasted productivity in economic terms. This limitation may diminish the utility of culturing cells for a wide range of potentially desirable uses including without limitation not only the study of drug toxicity or drug metabolism, but also therapeutic uses (such as a device comprising cultured cells that is used to treat patients), diagnostic uses (such as, for example, a device comprising cultured cells that is configured to measure some marker in the blood of a patient), or industrial uses (such as, to cite several examples, a device comprising cultured cells that is configured to test for the potential toxicity of molecules that are constituent elements of industrial or consumer products, or a device comprising cultured cells that is configured to test for levels of environmental pollutants or for the presence of chemical or biological warfare agents). With the cell culture systems described herein, this limitation is ameliorated and such uses as those elaborated above become more effective, cost-effective, and achievable. The embodiments presented herein contains various combinations of components and conditions in which the initial phase of low metabolic state is reduced providing quick achievement of highly functional and metabolically active cell cultures useful for a variety of purposes.

Described are multiple cell culture components. Each component of the system is distinct from the other components and each contributes to the unexpected benefits shown. Combinations of various cell culture components give rise to different embodiments. Also, each cell culture component may have one or more embodiments.

In one aspect, a cell culture component employed in compositions and methods described herein is a higher than normal atmospheric oxygen environment. This may include high oxygen conditions for seeding the cells and/or for the growth and culturing of the cells. High oxygen conditions or environment comprise a concentration of oxygen that is higher than a normally occurring, atmospheric concentration of oxygen. In one embodiment, the concentration of oxygen is about 50%, 55%, 60%, 65%, 70%, 75%, 80%, 85%, 90%, 95%, or 100% of the gaseous composition present in the system. In another embodiment, the concentration of oxygen is about 52%, 57%, 62%, 67%, 72%, 77%, 82%, 87%, 92%, or 97% of the total gaseous composition present in the system. In some instances the concentration of oxygen may be only slightly higher than the normal atmospheric concentration. The oxygen concentration may be held constant or relatively constant throughout the seeding or culturing, or it may be changed over the course of the seeding or culturing period.

There may be one or more non-essential gases present in the total atmospheric composition utilized for high oxygen conditions. The non-essential gas can be air, $CO_2$, $N_2$, or any type of inert gas.

High oxygen seeding is accomplished by a number of approaches. For example, high oxygen seeding is accomplished by seeding the cells in an air-tight culture chamber. In an exemplary embodiment, cells comprising a single cell type are seeded, i.e., plated, onto a suitable physical substrate and then placed in an air-tight chamber and the atmosphere is exchanged to high oxygen immediately following the seeding. Alternatively, high oxygen seeding can be accomplished by the use of a preconditioned chamber in which the chamber already maintains a high level or concentration of oxygen.

For high oxygen seeding, the duration in which oxygen level is maintained higher than atmospheric level may vary from as little as the time required for the seeding of the cell to as long as about 24 hours. In one embodiment, as soon as the seed culture is placed in a cell culture chamber, oxygen level is returned to normal atmospheric level. In another embodiment, the oxygen level is maintained higher than atmospheric level for 24 hours.

Alternatively or in addition, high oxygen conditions may be utilized after seeding. One could seed under normal oxygen concentration and then increase the gaseous level of oxygen for the period of time the cells are cultured. It is possible to utilize high oxygen conditions for cell culture, for about 1, 2, 3, 4, 5, 6, 7, 8 or more days, or for any greater or lesser length of time. In one embodiment, the high oxygen is used for seeding. In another embodiment the high oxygen is utilized for the entire culturing period. In another embodiment the high oxygen is utilized for a portion of the culturing period. In another embodiment the high oxygen is used intermittently.

For high oxygen conditions, the media can be treated by oxygen bubbling. The high oxygen conditions in the closed chamber may be accomplished just by utilizing oxygen bubbling through the medium. Alternatively, the media can be used without the bubbling. In one embodiment, the high oxygen content is achieved by increasing the partial pressure of oxygen in the gaseous environment in the cell culture device. It can be useful to begin with the high oxygen content or to close the system including the cells and then alter the oxygen content in the system. One may also enhance the oxygen concentration of the media by the addition of an oxygen carrier, such as hemoglobin or perfluorocarbon.

The level of oxygen can be monitored by various methods including blood gas analyzer, monitoring atmospheric tension, oxygen monitor, or other measuring devices known in the art. Monitoring of the oxygen will permit one to maintain the conditions at the desired oxygen level and for the period of time desired.

The oxygen level of the cell culture can be maintained by an automated feed-back regulator type device. For example, a computerized process can be employed to monitor the oxygen level and adjust the input oxygen level accordingly. Such devices are well known and available for this regulation.

In one aspect, a cell culture component is the absence of serum in the culture media. Alternatively, said cell culture component is low level of serum in the culture media. In one embodiment, the cells are cultured in serum-free or substantially serum-free media. A substantially serum-free medium might contain trace level of serum. Serum-free media can be prepared or purchased from material provided by serum-free media manufacturers. One example of such media is Dulbecco's Modified Eagles Medium. Serum-free media may include additives such as non-essential amino acids, antibiotics, L-glutamine, or tryptophan. In another embodiment, the cells are cultured in low-serum containing media. Examples of low serum concentration level include about 0.1%, 0.2%, 0.5%, 0.7%, 1%, 1.2%, 1.5%, 1.7%, 2.0%, 2.2%, 2.5%, 2.7%, 3.0%, 3.2%, 3.5%, 3.7%, 4.0%, 4.2%, 4.5%, 4.7%, 5.0%, 5.2%, 5.5%, 5.7%, 6.0%, 6.2%, 6.5%, 6.7%, 7.0%, 7.2%, 7.5%, 7.7%, 8.0%, 8.2%, 8.5%, 8.7%, 9.0%, 9.2%, 9.5%, 9.7%, 10%, 10.2%, 10.5%, 10.7%, or 11%, or any intermediate value between any of the forgoing. Alternatively, examples of low serum level include about 11%, 11.5%, 12%, 13.5%, 14%, 14.5%, 15%, 15.5%, 16%, 16.5%, 17%, 17.5%, 18%, 18.5%, 19%, 19.5% or 20% or any intermediate value between any of the forgoing.

Exemplary sources of serum include, but not limited to, horse, chicken, donkey, rabbit, cow, or rat.

In one aspect, a cell culture component is the use of material that allows the cells to assume three-dimensional ("3D") relationships to each other.

One approach for a 3D configuration comprises hepatocytes cultured in a "gel sandwich" configuration, wherein matrices of collagen fibers are configured both below and above the hepatocytes, and the hepatocytes are cultured in between the layers. In a variant 3D approach a monolayer of hepatocytes which is adhered to a rigid coated or uncoated surface is overlaid with a layer of collagen gel. A third 3D approach relies on the aggregation of hepatocytes into spheroids following the seeding of the cells on a soft gel such as Matrigel™ or a weakly adhering surface.

In an embodiment, the material that allows the cells to assume 3D relationships is a three-dimensional scaffold. The three-dimensional scaffold can be made with a biologically non-toxic, inert material. The scaffold can be made with material that allows cellular attachment. One example of such material is a biocompatible gel formula made with calcium alginate which forms a material for culturing the cells. Other examples of biological coating materials include, but are not limited to, methylcellulose, MATRIGELT™, BIOCOAT™, collagen, fibrinogen, fibronectin, gelatin, laminin hyaluronin, hyluronic acid, or any of the family of polyamines such as polylysines. Such materials encourage binding and enhance culturing and also may provide a micro-scaffold in which cells can multiply while maintaining three-dimensional relationship to each other. In one embodiment, the scaffold is made of a gel matrix. In another embodiment, the scaffold is self-assembling peptide hydrogel. In one embodiment there is no binding material on the scaffold. The cross-sectional dimensions of the structural filaments or fibers of the scaffold may range from 20 microns to 1000 microns, although any size that accommodates the cells, in the interstitial spaces of the scaffold, known as the pores, will generally function. Pore sizes may range in size from 1 micron to 200 microns, or larger.

In an aspect, the culture device includes one or more chambers at least one of which includes a physical structure containing a material for the three-dimensional cell culture. Such structure may be a microscale scaffold for the stable lodging of cellular material.

In a variant approach, hepatocytes can be entrapped in microscale scaffolds such as calcium alginate, inside which the hepatocytes may assume a three-dimensional configuration with respect to each other, such as a spheroid configuration. Yet other forms of 3D hepatocyte culture are comprised of culturing a slice or a segment of actual tissue drawn directly from the liver of a recently deceased organism; or an artificial tissue construct. 3D cell cultures may also comprise tissue slices or tissue segments drawn from other organs, such as slices or segments of brain tissue, or slices or segments of kidney tissue.

In one aspect, a cell culture component is a co-culture system. In one embodiment, a co-culture system comprises a first cell population and a second cell population wherein the second cell population plays a supportive role in the metabolic or other functionality of the first cell population. In an alternative aspect, each cell population's presence in the co-culture system serves to enhance the functionality of the other cell population and of the co-culture as a whole. Examples of such a supportive role include, but are not limited to, providing cytokines, providing cell-cell contact, providing anchorage, excreting or secreting extracellular material, and providing an environment mimicking the in vivo environment of the first cell population. The second cell population can be sublethally irradiated to prevent the population from growing. The second cell population can be a layer of cells attached to the planar surface of, or to a scaffold configured inside, the chamber. The second cell population can be configured to be cultured interspersed in or contiguous to the first cell population. Alternatively, the second population can be in suspension in the culture media. Exemplary sources of the second cell population include stromal cells, non-parenchymal cells, fibroblasts, glial cells, or immune cells. One can utilize various immune cells, such as lymphocytes, dendritic or Kupffer cells. In one embodiment, the second cell population is 3T3-J2 fibroblasts. In one embodiment, the first and second cell populations are from the same species of animal, such as human. In other cases, the cell populations are from different species. It may be useful to obtain the cells from any species of animal, including mammalian species such as human, monkey, mouse, rat, pig, cow, horse, dog or sheep. The cells may be freshly isolated cells, primary cells, engineered cells, preserved cells, a cell line, a tissue slice, a tissue segment, an artificial tissue construct, cryopreserved cells, or stem cells.

In one embodiment, the co-culture system is comprised of two different cell populations representing two different parenchymal cell populations or representing a parenchymal cell population and non-parenchymal cell population. For example, the first cell population can be a kidney glomerular parietal cell population and the second population can be a glomerular podocyte population. In another example, the first cell population can be hepatocytes, and the second population can be fibroblasts, endothelial cells, or stellate cells. The proportion between the first cell population and the second cell population can vary depending on the type of cells. The ratio can be about 1:1, 1:2, 1:3, 1:4, 1:5, 1:6, 1:7, 1:8, 1:9, 1:10, or vice versa, or any intermediate ratio between any two of the foregoing, or any other ratio. In one embodiment, hepatocytes are cultured with 3T3-J2 fibroblasts in a 10:1 ratio. In another embodiment, hepatocytes are cultured with 3T3-J2 fibroblasts in a 2:1 ratio. In yet another embodiment, hepatocytes are cultured with 3T3-J2 fibroblasts in a 1:1 ratio. Another example is a gut epithelial population and a goblet cell population. Another example is a Type I pneumocyte population and an endothelial cell population. In another example the first population is a keratinocyte population and the second population is a Langerhan cell or dendritic cell population. In one embodiment, the co-culture system is comprised of three or more different cell populations representing parenchymal cell populations, non-parenchymal cell populations, and immune cell populations; for example, the first cell population can be hepatocytes; the second population can be fibroblasts, endothelial cells, or stellate cells; and the third population can be Kupffer cells or T cells. Another example of a co-culture comprising three or more different cell populations is a kidney glomerular parietal cell population, a glomerular podocyte population, and an endothelial cell population. Another such example is a co-culture comprising a keratinocyte population, a fibroblast population, and a Langerhan cell or dendritic cell population. Another such example is a gut epithelial population, a goblet cell population, and a T cell population. Another example is a Type I pneumocyte population, a Type II pneumocyte population, and an endothelial cell population. In one embodiment, members of the respective cell populations are configured to be cultured in a particular geometric arrangement and/or in particular proportions to one another by means of a micropatterning technique.

A variety of configurations of the physical substrate for adhering, holding or containing the cell culture system are possible, including a flat substrate; or, in an embodiment, the physical substrate may be configured to comprise at least one chamber or compartment. The chamber comprises a planar surface and walls surrounding and partially or completely enclosing the planar surface. The planar surface is coated or treated to allow cellular attachment. In an aspect, the chamber is open in one dimension, thereby assuming the configuration of an open compartment or well. In an alternative aspect, the chamber further comprises an additional element configured to be continuously contiguous with the walls of the chamber, so as to comprise a closed, air-tight chamber suitable for the containment, without leakage, of gaseous or liquid cell culture medium. The cell culture chamber is structured to contain media as well as to withstand atmospheric pressure accompanied with oxygenation. The chamber may or may not comprise at least one opening through which sampling of the media or atmosphere can be performed, or through which cell culture medium can enter and/or exit the chamber, thereby perfusing any cellular materials configured therein. In an embodiment, the cell culture chamber is microscale, wherein microscale means being configured to possess at least one physical feature that is characterized by having at least one linear dimension (length, width, height or depth) measuring less than one millimeter. Often microscale is considered to be having dimensions of 10 nm to 1 mm In an aspect, for ease and efficiency of use, the cell culture chamber is repetitively configured with multiple embodiments integrated proximally one to another into a single piece of laboratory ware, such as a multi-well microtiter plate.

In one embodiment, a cell culture chamber can be used to accommodate a monolayer cell culture. In an alternative embodiment, the cell culture chamber is used to accommodate a cellular co-culture, a culture of cells in a 3D configuration, subcellular materials, cellular products, or subcellular components, any of which may be primary, naturally occurring, man-made, artificial, or engineered. The subcellular material in the culture device may be a cellular product. Exemplary cellular products may include without limitation an enzyme, a nucleic acid, a protein, a lipid, and a carbohydrate. The cellular product may be man-made. The cellular product may comprise a naturally occurring or man-made cellular product in conjunction with some other biochemical entity. The subcellular material may comprise a subcellular component. Exemplary subcellular component may include without limitation a microsome, mitochondrion, nucleus, ribosome, plasma membrane, and the like. The subcellular component may be man-made. The subcellular component may comprise a naturally occurring or man-made subcellular component in conjunction with some other biochemical entity. For example, the subcellular component may be an engineered enzyme, protein or artificial cellular structure. Such subcellular component may be included in any of the compartments during the culturing step. In one embodiment, the subcellular component is involved in the metabolic or toxicological process of the system. For example, a material to be analyzed may be cultured with the first population of metabolically active cells to produce a product from the culturing step, which may interact with the subcellular component. The result of that interaction may be measured or analyzed to provide an evaluation of the material.

In another embodiment the physical substrate for cell culture is a biochip. The biochip comprises a microscale channel or channels fluidically connected to or otherwise fluidically integrated with at least one chamber or compartment for culture of cells or subcellular materials. The at least one channel and the at least one chamber are configured to facilitate the actuated, microfluidic circulation or recirculation of cell culture medium in contact with or in proximity to the cell culture system, under a condition of perfusion or flow. In an aspect the configuration of the at least one compartment and the at least one chamber comprises a linear flow path for the circulation or recirculation of the cell culture medium. In an alternative embodiment the flow path may bifurcate and become multilinear. The biochip may be microscale. The at least one compartment of the biochip may be configured to be either open in one dimension, thereby assuming the configuration of an open compartment or well; or closed so as to comprise a closed, air-tight chamber suitable for the containment, without leakage, of gaseous or liquid cell culture medium, as well as to withstand atmospheric pressure accompanied with oxygenation. In an aspect, the chamber also comprises an inlet and an outlet for flow of culture medium.

An embodiment of the biochip may contain a single compartment (e.g., a chamber); or alternatively, another embodiment of the biochip may contain two compartments, where one compartment contains cells, subcellular materials, subcellular components, or cellular products and the other compartment is an open reservoir for the addition or withdrawal of culture medium. In another aspect, more than one chamber of the biochip may each contain cells cultured in a monolayer, cells cultured in a co-culture, subcellular materials, subcellular components, or cellular products, wherein the cell culture system contained in one chamber is different from the cell culture system contained in the at least one other chamber. In an alternative embodiment, the cell culture system in one compartment of the biochip is identical to the cell culture system in the at least one other compartment of the biochip. In another embodiment the biochip may contain at least one compartment and in some instances three or more compartments.

Another embodiment of the biochip may further comprise a pumping mechanism, wherein the pumping mechanism may either be integrated in the biochip or separate from and external to the biochip. In one such embodiment the pumping mechanism may be hydraulic, such as a syringe pump or a peristaltic pump. In one such embodiment, the pumping mechanism may be electro-kinetic or, alternatively, an alternative embodiment may comprise a diaphragm pump that is mechanically actuated or pneumatically actuated. In another embodiment, the biochip may further comprise a de-bubbler located within the biochip or external to the biochip. In another embodiment the biochip may comprise at least one sensor for obtaining signals from the cultured cells, subcellular materials, subcellular components, or cellular products, wherein at least one sensor may be a biosensor and the biosensor may comprise a waveguide.

The biochip may be microfabricated. The biochip may be manufactured from a microfabricated master. The biochip may be manufactured by mass production that causes the geometry of the device (including the provision for the rate of fluid flow in and through the device) to be substantially the same from one such manufactured copy, specimen or iteration of the device to the next. The process of mass production may include that the biochip is manufactured from a microfabricated master.

The well, chamber, microtiter plate, biochip, or other physical substrate may be comprised of glass, silicon, a plastic such as polycarbonate, cyclic oxide copolymer (COC), polystyrene, or other plastic formulations, or any other material that may comprise a suitable physical substrate for in vitro cell culture.

In one aspect, a cell culture component employed in compositions and methods described herein is cell culture medium that is configured to come into contact or proximity with a cell culture system under a condition of perfusion or flow. The biochip, the cell culture system and the pump may be configured together to achieve desired or optimal levels of metabolic or other cellular functions under the at least one condition of perfusion or flow. The condition of perfusion or flow may be configured to maintain desired values or ranges of certain parameters, such as the amount of shear stress brought to bear upon the cells by the perfusate culture medium, the flow volume or flow velocity of the perfusate culture medium as it contacts or comes into proximity to the cell culture system, the residence time during which a single molecule of a chemical entity dissolved or suspended in the perfusate culture medium remains within a compartment of the biochip or remains in contact with the at least one cell culture system contained in the biochip, and the like. Maintaining desires values or ranges of these and other parameters may cause the cell culture system to manifest desired or optimal levels of cellular function. In one aspect, a desired value or range of at least one such parameter simulates a value found in a living organism.

In an embodiment, the condition of perfusion or flow is maintained during cell seeding. In an alternative embodiment, the condition of perfusion or flow is maintained during cell culture. Parameters that characterize the flow may be controlled so as to achieve desired or optimal levels of cellular or subcellular functionality. For example, in an embodiment the shear stress exerted by the flowing cell culture medium upon the cell culture system is less than 14 dynes per square centimeter ($dyn/cm^2$). In an alternative embodiment the shear stress exerted by the flowing cell culture medium upon the cell culture system is less than 2 $dyn/cm^2$. In other embodiments, the shear stress exerted by the flowing cell culture medium upon the cell culture system and cells is less than 1 $dyn/cm^2$, less than 0.5 $dyn/cm^2$, less than 0.2 $dyn/cm^2$, less 0.1 $dyn/cm^2$, less than one order of magnitude less than 0.1 (0.01) $dyn/cm^2$, less than two orders of magnitude less than 0.1 (0.001) $dyn/cm^2$, less than three orders of magnitude less than 0.1 (0.0001), less than 0.00001, less than 0.000001 $dyn/cm^2$, less than 0.0000001 $dyn/cm^2$, less than 0.00000001 $dyn/cm^2$, less than 0.000000001 $dyn/cm^2$, less than 0.0000000001 $dyn/cm^2$. In another embodiment, the cell culture system is configured in a biochip and the at least one compartment of the biochip is in turn configured with a series of ridges and depressions in its planar surface, such that the cell co-culture is seeded down in the depressions of the compartment while the ridges, which extend higher up into the flow path than the cell culture system does, serve to mechanically shield the cell culture system from the most forceful contacts with the perfusate, such that the shear stress exerted upon the cell culture system is minimal. In an alternative aspect, the compartment is configured to comprise a permeable membrane that segregates the cell culture system from the flowing perfusate and thereby shields it from shear stress while permitting chemical entities dissolved or suspended in the perfusate culture medium to come into contact and interact with the cell culture system by diffusing across the membrane. In another aspect, the flow rate of the perfusate cell culture medium through the biochip is two nanoliters per minute (2 nL/min). In an alternative aspect, the flow rate of the perfusate is five microliters per minute (5 µL/min) In a third exemplary aspect, the flow rate is one milliliter per minute (1 mL/min) In another embodiment, the flow rate is any intermediate value between any of the foregoing rates. The flow rate may be held constant or, in an alternative embodiment, it may vary or be intermittent during the period of cell culture or during the period of cell seeding. In another embodiment, the geometry of the biochip design and the speed of the pumping mechanism are together configured to produce a residence time in the at least one compartment of the biochip of about 0.5 seconds (sec.), 0.75 sec., 1.0 sec., 5.0 sec., 20 sec., 30 sec., 60 sec., 2 minutes (min), 5 min, 30 min, 60 min., 2 hours (hr.), 3 hr., 4 hr., 6 hr., 12 hr., 24 hr., 48 hr., 96 hr., 1 week (wk.), 2 wk., or any time value between any of the foregoing. In one aspect, the residence time is configured to simulate at least one residence time found in vivo in the human liver.

An example of an embodiment that comprises the multiple cell culture components is high oxygen seeding in the presence of 95% oxygen; cell culture media comprising a low concentration of serum; non-parenchymal cells as the second cell population; and cell culture medium that is configured to be pumped so as to re-circulate through the compartment, where it comes into contact with cells from at least one of the cell populations under at least one condition of perfusion or flow. In another embodiment, an example of the multiple cell culture components is high oxygen seeding in the presence of 87.5% oxygen, cell culture medium comprising no serum, non-parenchymal cells as the second cell population, and cell culture medium that is configured to perfuse the cell culture system in a biochip at a rate of 5 mL/min. Alternatively, the cell culture system comprises multiple cell culture components comprising high oxygen seeding in the presence of 95% oxygen, cell culture media with 0.5% serum concentration, non-irradiated fibroblasts as the second cell population, and a three dimensional cell culture scaffold—including a layer of a binding material, such as MATRIGEL™. Another alternative example of the multiple cell culture components comprises high oxygen seeding in the presence of 100% oxygen, cell culture media with 1% serum concentration, a co-culture comprising cryopreserved primary human hepatocytes as the first cell population and 3T3-J2 fibroblasts as the second cell population, and flowing cell culture medium that perfuses the co-culture (configured in a compartment of a biochip) while maintaining a residence time in the compartment similar to at least one value for residence time obtained in vivo in the liver of an adult human, and while exerting in the compartment a shear stress of less than 2 dyn./$cm^2$. Another embodiment includes high oxygen culturing in 95% oxygen, cell culture media in serum free media, non-irradiated fibroblasts as the second cell population, and a three dimensional cell culture scaffold including a layer of a binding material, such as MATRIGEL™.

In one embodiment, the cell culture system comprises multiple cell culture components. One example of the multiple cell culture components includes high oxygen seeding in the presence of 95% oxygen, serum-free cell culture media, non-irradiated fibroblasts as the second cell population, and a cell culture scaffold provided by MATRIGEL™. Another example of the multiple cell culture components is high oxygen seeding in the presence of 100% oxygen, serum-free cell culture media, 3T3-J2 fibroblasts as the second cell population, and a cell culture scaffold provided by MATRIGEL™. Yet another example of the multiple cell culture components is high oxygen seeding in the presence of 95% oxygen and 5%

$CO_2$, serum-free media, 3T3-J2 fibroblasts as the second cell population, a cell culture scaffold provided by collagen coating.

In another embodiment, the cell culture the system comprises three cell culture components. One example of the three cell culture components are high oxygen seeding in the presence of about 95% oxygen, serum-free cell culture media, and non-irradiated fibroblasts as the second cell population. Another example of the three cell culture components are high oxygen seeding in the presence of 100% oxygen, serum-free cell culture media, 3T3-J2 fibroblasts as the second cell population. Yet another example of the three cell culture components are high oxygen culturing in the presence of about 95% oxygen and about 5% $CO_2$, serum-free cell culture media, 3T3-J2 fibroblasts as the second cell population.

In one embodiment, the cell culture the system comprises two cell culture components. One example of the two cell culture components is high oxygen seeding in the presence of 95% oxygen and cell culture media with serum-free media. Another example of the two cell culture components is high oxygen seeding in the presence of 100% oxygen and cell culture media with 0.1% serum. Yet another example of the two cell culture components is high oxygen culturing in the presence of about 95% oxygen and about 5% $CO_2$ and serum-free cell culture media.

It is possible to use any mammalian cell type, whether comprising a primary cell or a cell line, for the cultures, including without limitation hepatocytes, enterocytes, keratinocytes, neural cells, cardiac muscle cells, pancreatic cells, renal cells, and stem cells. Various embodiments of the culture system disclosed herein can be customized as to cell type so as to obtain a high metabolic or other functional state of the cells from close to the onset of the culture; or to obtain at least one other unexpected benefit from the culture. Compositions and methods described herein can be useful for maintaining for an extended period of time primary cell culture, i.e., cells freshly isolated from tissue or an organ; or alternatively for maintaining for an extended period of time cell lines, i.e., engineered cells adapted to grow and/or be maintained and to function under in vitro conditions.

Primary cells can be obtained by any techniques known in the art. Examples of such techniques include but are not limited to surgical separation, isolation, fluorescence activated cell sorting, magnetic activated cell sorting, use of a cell sieving device, centrifugation, volume cell sorting, and chemotactic cell sorting methods. In practice one may utilize multiple-parallel formats wherein the format allows parallel culturing of cells under the disclosed different combinations of cell culture components. In one embodiment, the format is implemented in a micro-titer plate. Examples of micro-titer plates include 6-well plate, 12-well plate, 24-well plate, 48-well plate, 96-well plate, 256-well plate, 384-well plate, and 1536-well plate.

Compositions and methods described herein can be manufactured as a kit. In one embodiment a kit comprises a microtiter plate, oxygen tank containing a mix of gases with predetermined ratio of high oxygen content, frozen vials containing one or more cell population(s), and serum-free or low serum culture media. In one embodiment a kit comprises a microtiter plate coated with a binding agent and lyophilized cells and serum-free or low serum media. In another embodiment the kit comprises a microfluidic chip including channels for circulation of media to permit contacting the cells under perfusion or flow, one or more compartments for culturing cells, which compartments may include a variety of designs and materials, such as biocompatible coatings of binding agents, scaffolds for three-dimensional cell growth, reservoirs for fluids, and ports for the injection of materials, gases, and monitoring of oxygen or metabolic activity and products. Such chip may include cells and media. Alternatively, the kits may include the chip, vials of the primary and secondary cells and media for cell growth. The kit may also include educational or training materials such as an instruction manual or CD.

A variety of methods may be used to measure the metabolic, toxicological, or other functional state of the cells. Methods of measurement include any method to measure gene expression (e.g. reverse transcription polymerized chain reaction ("RT-PCR") analysis), any method to measure the expression level of enzymes or other proteins produced in or by the cell (e.g. western blot or ELISA), any method to measure the activity of enzymes or other proteins produced by the cell (e.g. EROD (ethoxyresorufin-O-deethylase), MROD (methoxyresorufin-O-deethylase), PROD (pentoxyresorufin-O-deethylase), BROD (benzyloxyresorufin-O-deethylase) assays, or metabolite formation by liquid chromatographic/mass spectroscopic analysis), any method to measure active molecular transport into or out of the cell, any method to measure the metabolic activity of organelles such as mitochondria, any method to measure the production or secretion of cytokines or chemokines, any method to measure the presence or quantity of a biomarker indicative of a toxicological, signaling, or other cellular process, or any other method used to measure an aspect of cellular functionality. In one embodiment, hepatocytes are cultured in a culture system comprising multiple cell culture components and their metabolic states are measured by the level of albumin. In another embodiment, hepatocytes are cultured in a culture system having two, three or multiple components for three days and their collective metabolic state is measured by reverse transcription polymerized chain reaction ("RT-PCR") analysis. In one embodiment, hepatocytes are cultured for a period of one, two, three, or four days, or longer, in a culture system having two, three or multiple components, in the presence of a potential toxicant dissolved or suspended in the culture medium, and the cells and the culture medium are subsequently assayed to determine the presence of a biomarker indicative of the onset of an apoptotic or otherwise cytotoxic process having incepted in the cell. In some embodiments, the system may include five cell components—serum free media, higher than atmospheric oxygenation, co-culture in a 3D structural relationship and perfusion of the culture media. In one embodiment, primary enterocytes or CACO-2 cells are cultured for a period of one, two, or three days, or longer, in a culture system having two, three or multiple components, in the presence of a molecular entity dissolved and suspended in the culture medium, wherein the primary enterocytes or CACO-2 cells are cultured on a physical substrate that is configured with the enterocytes or CACO-2 cells as a permeable membrane; and the cells and the culture medium are subsequently assayed to determine the metabolic action of CYP3A enzymes expressed in said cells upon said molecular entity; and also to determine whether the cells have afforded the absorption of the molecular entity through the permeable membrane. In an embodiment, primary glomerular cells isolated from a human kidney are cultured for a period of one, two, or three days, or longer, in a culture system having two, three or multiple components, in the presence of a molecular entity dissolved and suspended in the culture medium, and the cells and the culture medium are subsequently assayed to determine the presence of a biomarker indicative of the onset of an apoptotic or otherwise nephrotoxic process having incepted in the cell.

The devices and methods disclosed herein can be useful for drug discovery and development or for consumer and industrial product testing, or for environmental testing or biodefense applications. Such testing includes, but is not limited to in vitro drug toxicity testing and in vivo-surrogate testing. In one embodiment, the culture systems described herein is used for the study of drug clearance. In one embodiment it is used for the study of metabolite generation. In one embodiment it is used for the study of mechanisms of active or passive molecular transport. In one embodiment it is used for the testing of the toxicity of substances constituent to consumer products such as toothpaste, shampoo, hair dye, or makeup. In one embodiment it is used for the testing of the toxicity of substances constituent to industrial products such as paint or insulation materials. In one embodiment it is used for measuring the level of environmental pollutants such as dioxin. In one embodiment, an environmental sample is extracted from water or atmosphere and introduced into a culture medium, where it may subsequently incite in the cell culture a response indicative of toxicity, inflammation or hypersensitivity. In one embodiment it is used for detecting the presence of a chemical or biological warfare agent, such as aflatoxins. With the disclosed cell culture systems, enhanced cellular function is manifested with respect to at least one type of cellular function to produce a higher percentage of the functionality that the cells would evidence in vivo, compared to what those cells could produce under in vitro cell culture conditions that were not so enhanced.

Alternatively, enhanced cellular functionality may comprise the greater speed, or rapidity—i.e., the reduced time required—in which cells may recover an equivalent degree of any one such type of cellular functionality compared to the time in which those cells could recover that same functionality under in vitro cell culture conditions that were not so enhanced. The benefit of such time-based enhanced cellular functionality is that it may increase the aggregate amount of time during which the cell manifests the full level of functionality it achieves in in vitro culture, or diminish the time that elapses during the cell or tissue culture process, before that high level of full in vitro functionality incepts, thereby increasing the total time available, and therefore, the total potential benefit derivable, from the cell culture while in subsequent experimental use. In an alternative aspect the benefit of such time-based, enhanced cellular functionality is that it minimizes the time that is lost, and the attendant labor and cost that is expended, compared to cell culture methods that do not benefit from the enhanced functionality yielded by compositions and methods described herein, which require longer periods of time in culture.

The systems may be utilized to evaluate the toxicity, efficacy, and pharmacokinetic disposition of new drugs more efficiently than is currently possible because of the quicker achievement of a high metabolic state by the cells. One aspect of the culturing systems disclosed is the ability to detect the formation, accumulation and/or further metabolic clearance of secondary metabolites as well as the potential to elucidate the role of drug transporters in drug clearance. For example, a parent molecular entity can be exposed to the system and the culture medium can subsequently be repeatedly sampled at predetermined time points; the samples can then by analyzed by mass spectroscopy to investigate the prospective formation and clearance of primary metabolites of the parent, secondary metabolites of the parent, tertiary metabolites of the parent, and subsequent generations of metabolites of the original parent compound.

EXAMPLES

Exemplary Cell Culture System Comprising Multiple Cell Culture Components

The system depicted in FIG. 1 comprises a compartment 102 with a layer of binding material 103 configured to facilitate the physical adherence of cellular materials to the physical substrate 101. The binding material 103 is comprised of at least one material drawn from the group consisting of MATRIGELT™, any of the cell culture systems provided under the trade name BIOCOAT™, collagen, fibrinogen, fibronectin, gelatin, laminin hyaluronin or hyaluronic acid, or any of the family of polyamines such as polylysines. The system 100 depicted in FIG. 1 also comprises a co-culture of at least one type of metabolically active cell 104 located in proximity with at least one type of non-parenchymal, stromal cell 105. The system 100 depicted in FIG. 1 also comprises a liquid cell culture medium containing no serum 106 and a cell culture environment 107 having an oxygen content higher than atmospheric concentration.

The system depicted in FIG. 1A illustrates an alternative embodiment of the system. Hepatocytes 104 and fibroblasts or other types of stromal cells 105 are affixed in a particular geometry and proximity to each other within a compartment 102 on the physical substrate 101 in predetermined quantities and patterns using a micropatterning technique. Binding material 103 is selectively placed so as to cause the cells 104 and 105 to assume their desired positions and geometry in the micropattern. The system 100 depicted in FIG. 1A also shows a liquid cell culture medium containing no serum 106 and a cell culture environment 107 having an oxygen content higher than atmospheric concentration.

Figure 2:
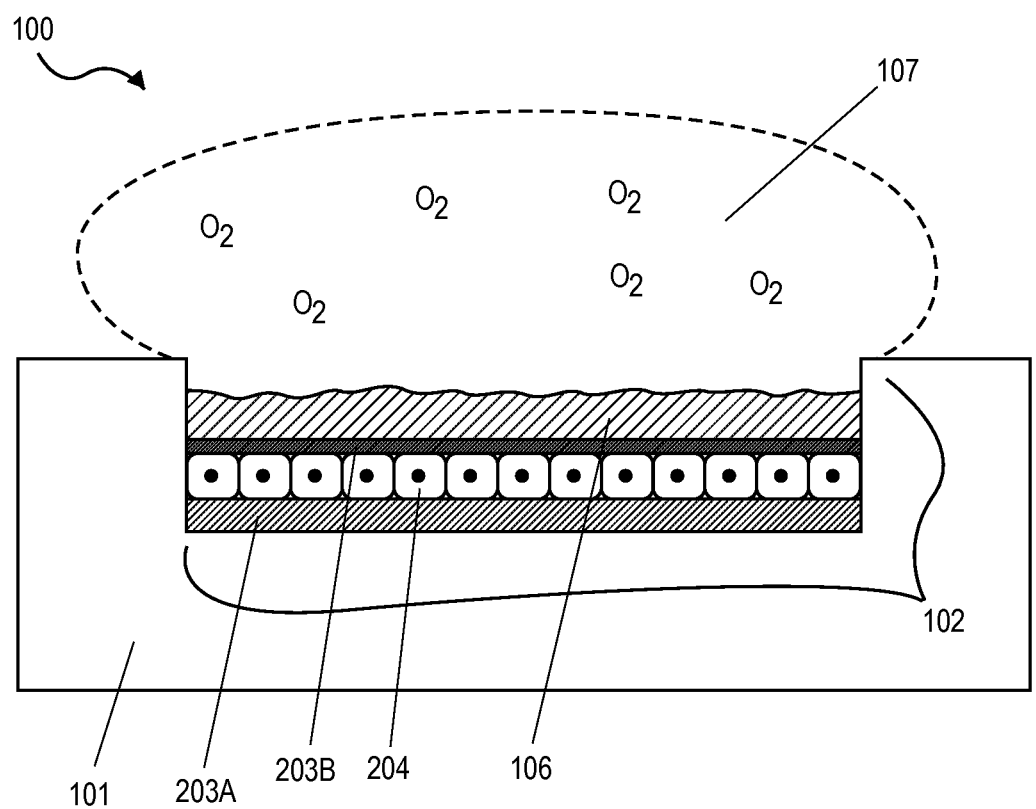
FIGS. 2 and 2A is illustrates an embodiment of compositions and methods described herein comprising multiple cell culture components.

FIG. 2 illustrates an alternative embodiment of the system. The system 100 depicted in FIG. 2 comprises protein layers 203A and 203B that are configured above and below the metabolically active cells 204 that are configured in a monolayer between them. The protein layers 203A and 203B and the metabolically active cells 204 collectively comprise a type of three-dimensional cell culture configuration. Alternatively, the lower protein layer 203A may not be not present while the upper protein layer 203B is configured to be present in the system, comprising along with the cells 204 a type of three-dimensional cell culture configuration. In yet another embodiment of the system 100, the lower protein layer 203A is not present but in its place is configured a layer of binding material 103 within the compartment 102 of the substrate 101. Also shown are the system 100, a liquid cell culture medium 106 and a cell culture environment 107 having an oxygen content higher than atmospheric concentration.

Figure 2A:
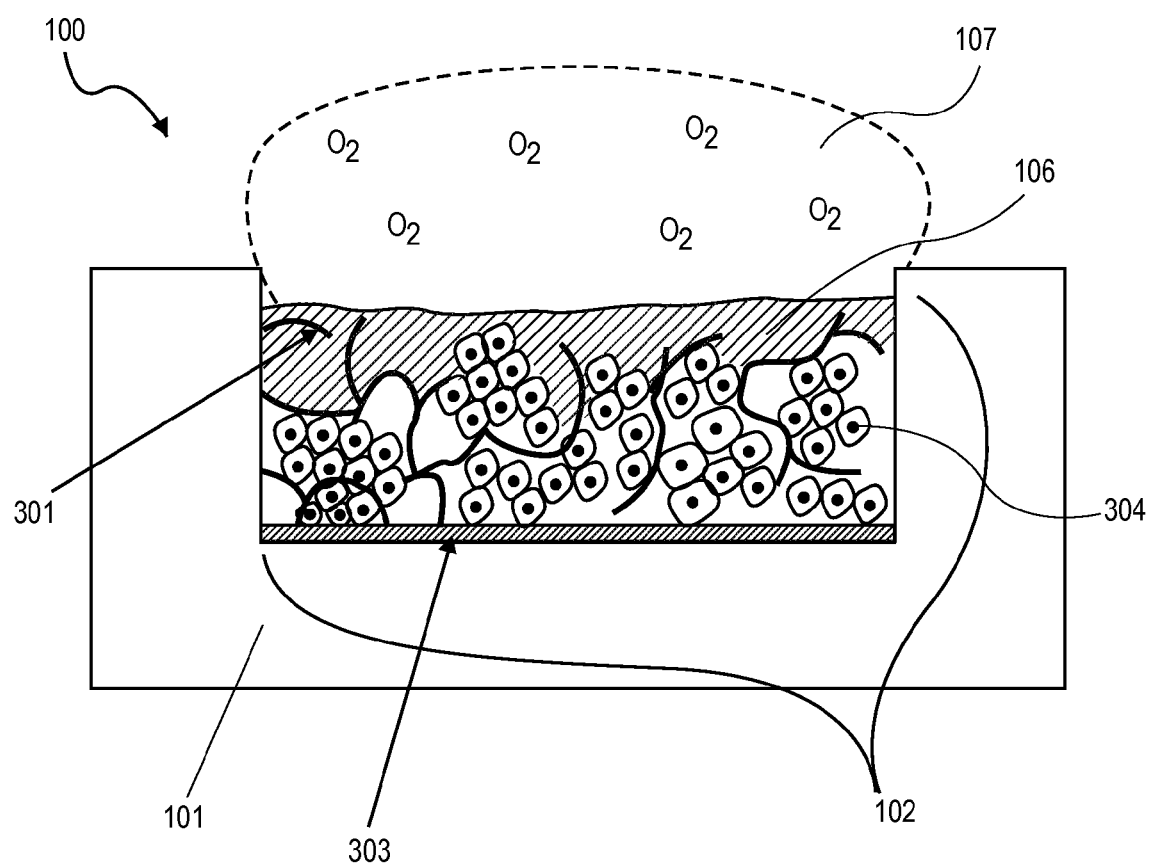

FIG. 2A illustrates an alternative embodiment of the system. The at least one compartment 102 of the physical substrate 101 contains a material that is configured to comprise a type of three-dimensional cell culture microscale scaffold 301 for the stable lodging and/or adherence of cellular material. The scaffold 301 may be comprised of calcium alginate. The cross-sectional dimensions of the scaffold 301 may vary in size. A protein binding material 303 is configured to affix and stabilize points of the scaffold 301 to the compartment 102. Alternatively, protein binding material 303 may be absent. Metabolically active cells 304 are configured to be lodged and stabilized in the pores of the scaffold, agglomerating into non-linear configurations of multiple cells such as (but not limited to) spheroids. Also shown are the system 100, a liquid cell culture medium 106 and a cell culture environment 107 having an oxygen content higher than atmospheric concentration.

Figure 3A:
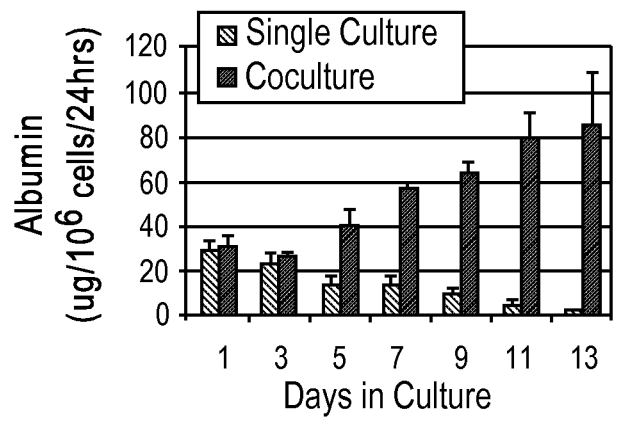
FIGS. 3A and 3B illustrates effects of various cell culture components on the metabolic state of cultured cells.
Figure 3B:
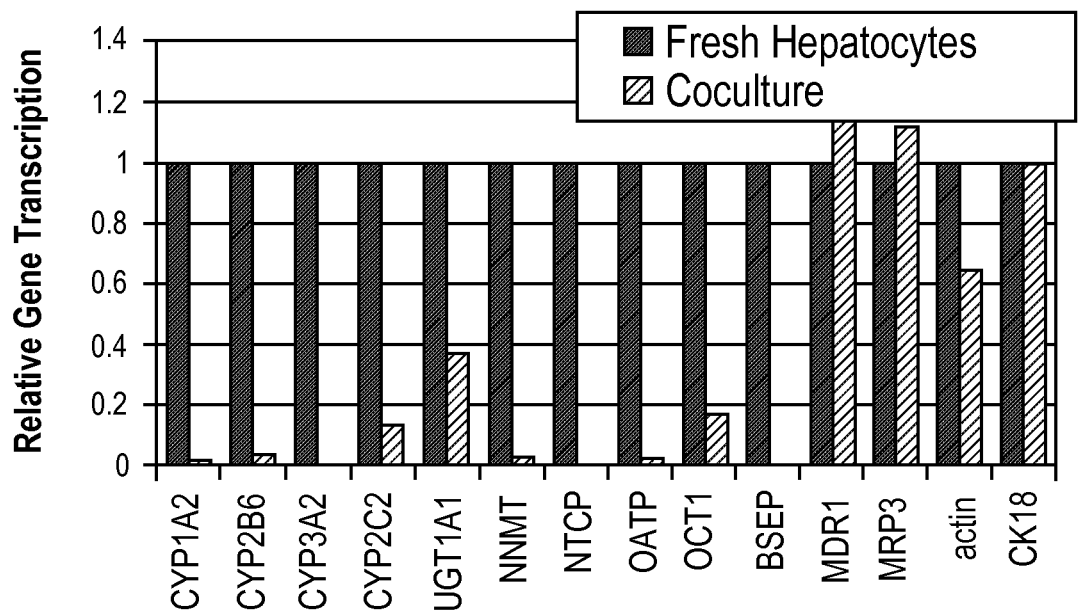

Effect of Various Cell Culture Components on the Metabolic State of Cultured Cells In FIGS. 3A and B, freshly isolated hepatocytes are co-cultured with 3T3-J2 fibroblasts, in the presence of serum-containing media and atmospheric oxygen. Albumin production slowly increases over time stabilizing at 80 μg/1×10$^6$ cells/24 hrs following 11 days of co-culture. Gene expression analysis of Phase I and Phase II enzymes such as CYP450 enzymes in the case of Phase I enzymes, or glucuronidation enzymes or sulfation enzymes in the case of Phase II enzymes], as well as transporter proteins is carried out by quantitative reverse transcription polymerase chain reaction (qRT-PCR). Gene expression at the onset of culture is minimal and is significantly lower than in vivo levels of transcription.

Figure 4A:
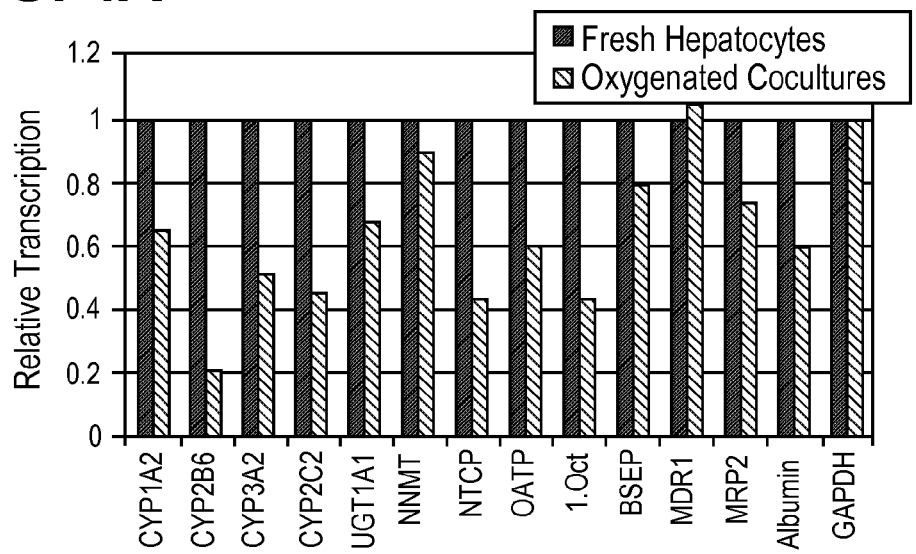
FIGS. 4A, 4B, and 4C illustrates effects of various cell culture components on the metabolic state of cultured cells.

In FIG. 4A, the gene expression of hepatocytes co-cultured with non-parenchymal cells in serum free media, and under high oxygen tensions (95% $O_2$, 5% $CO_2$) at the first day of culture (Day 1), is compared to that of fresh hepatocytes. Gene expression analysis of phase I and phase II enzymes, as well as transporter proteins is carried out by quantitative reverse transcription polymerase chain reaction (qRT-PCR). Gene expression at the onset of culture is comparable to in vivo levels of gene transcription.

Figure 4B:
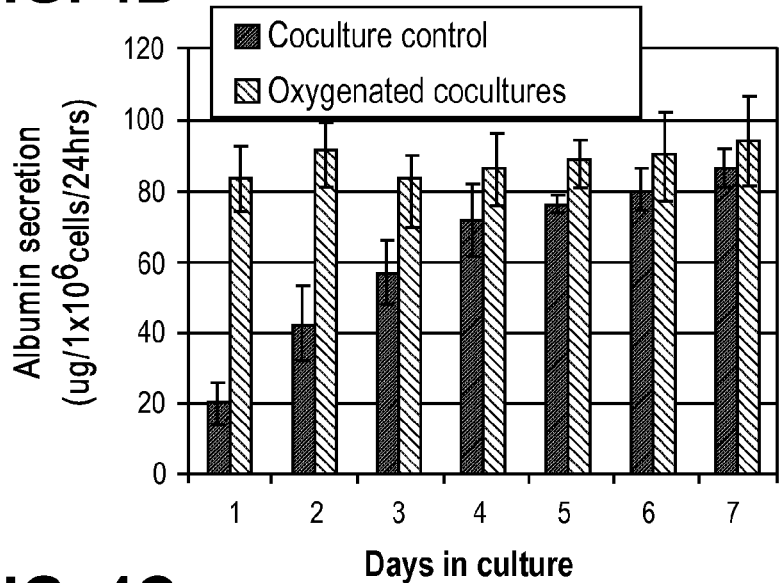
Figure 4C:
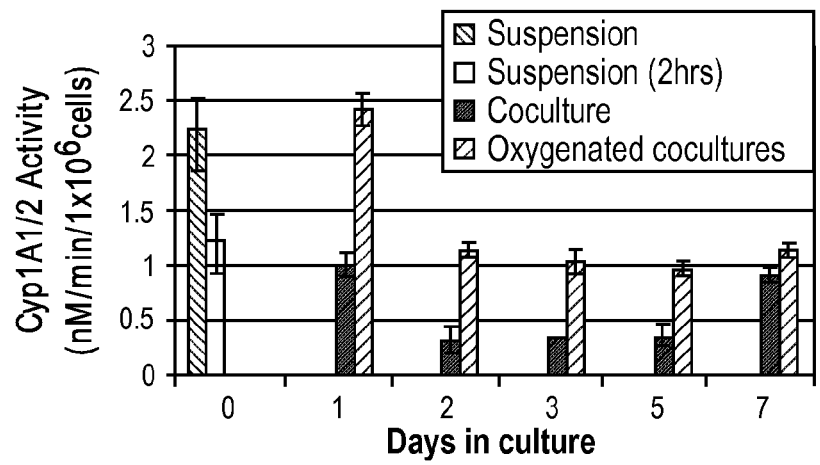

In FIG. 4B, long-term synthetic function of oxygenated cultures is tested. In FIG. 4C, long-term cyp1A1/2 activity is measured. During the first day of culture, albumin secretion is 4-fold higher in oxygenated, serum-free, co-cultures compared to hepatocytes co-culture with 3T3-J2 fibroblasts under standard conditions (P=0.011 N=3) demonstrating the more rapid achievement of metabolic function. No significant difference is detected at day seven of culture. To compare long-term cyp1A1/2 activity to hepatocytes in suspension, freshly isolated hepatocytes as described above is compared to isolated hepatocytes following 2 hours of incubation at 37° C. to control for the rapid loss of function in suspension. FIG. 4C shows that cyp1A1/2 activity in oxygenated cultures is comparable to that of hepatocytes in suspension. During the first day of culture, the activity is 135% higher than that of hepatocytes co-cultured with 3T3-J2 under standard conditions (P=0.001 N=3). However, at day 7 of culture, there is no significant difference between the cultures, demonstrating a benefit of the combinations.

Clearing of Drugs in Hepatocytes Cultured According to One Embodiment

Figure 5A:
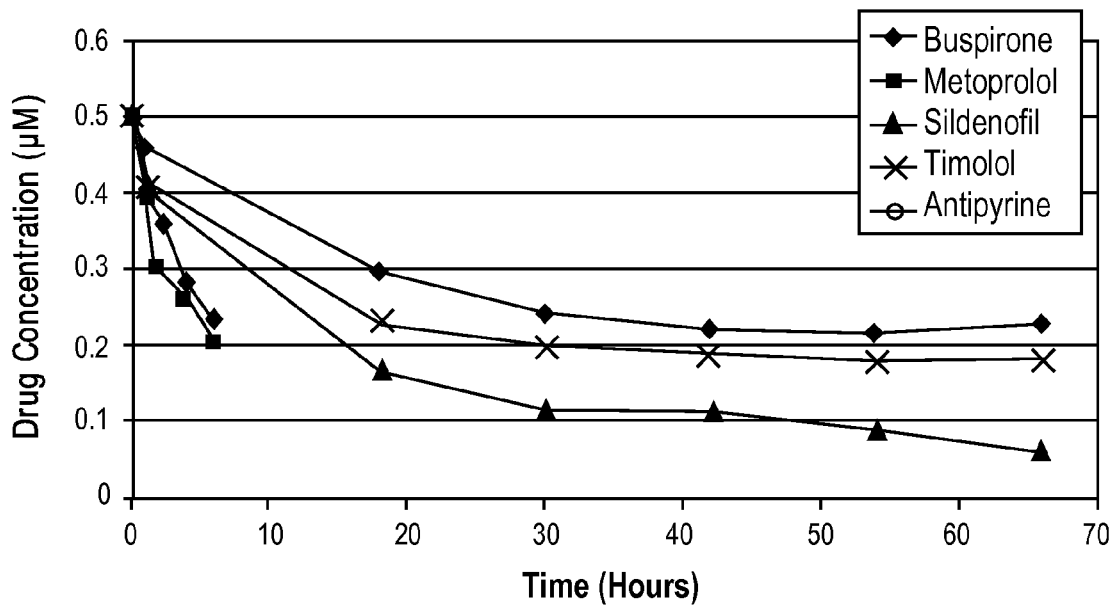
FIGS. 5A and 5B illustrates clearing of drugs by hepatocytes cultured according to one embodiment of present invention.
Figure 5B:
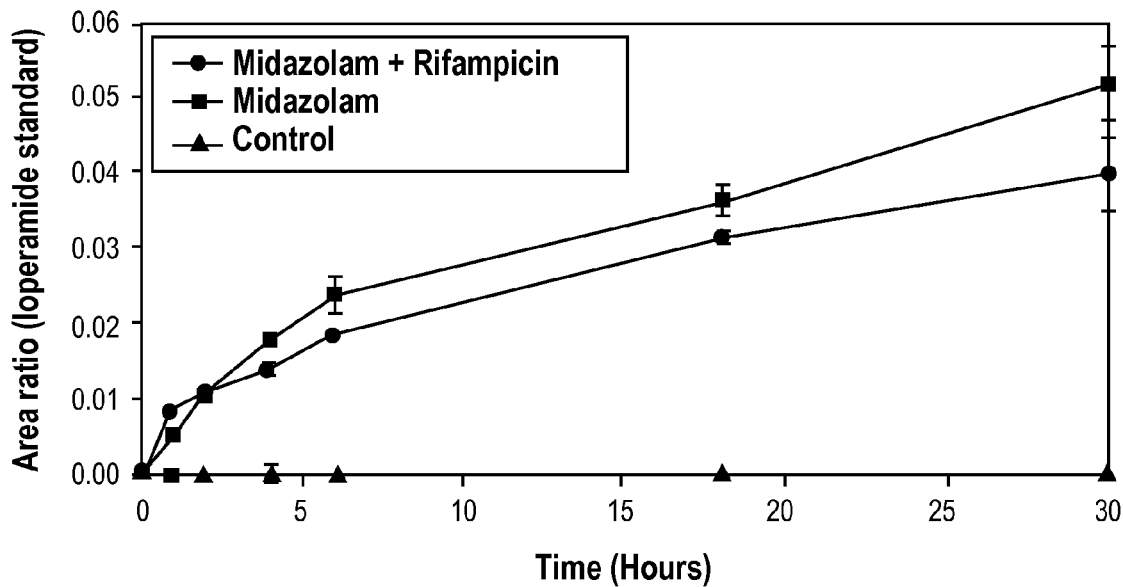

Cryopreserved human hepatocytes are cultured with 3T3-J2 fibroblasts under serum free conditions. Following overnight incubation in high oxygen tension (95% $O_2$, 5% $CO_2$) the cells are exposed to one of the following drugs: antipyrine, buspirone, metoprolol, sildenafil, and timolol. FIG. 5A shows the clearance of all drugs including slow clearing drugs such as antipyrine, sildenofil, and timolol which could not be assayed using suspension cultures. FIG. 5B shows the long term accumulation of 4-OH midazolam in our cultures in the presence and absence of rifampicin an inhibitor of the drug transporter Oatp-2. The accumulation of 4-OH midazolam in the culture media can be detected over 30 hours of culture. This allows the completion of long term experiments and evaluations during the first few days of culture.

High Metabolic State of Hepatocyte at the Onset of Cell Culture

High metabolic state may comprise the cell's enhanced ability to synthesize proteins or other cellular products; to maintain the functionality of organelles or other subcellular components, such as mitochondria; to produce cytokines; to express genes; or to transport or metabolize xenogenous materials with which the cell comes in contact; or to perform any other cellular function High metabolic state may comprise the degree, or extent, to which the cell manifests any of the foregoing functions. High metabolic state may therefore be manifested by cell culture systems the unique configurations of which endow their constituent cells with the ability with respect to at least any one type of cellular function to produce a higher percentage of the functionality that they would evidence in vivo, compared to what those cells could produce under in vitro cell culture conditions that were not so enhanced.

Table 1 illustrates the advantages of the transition to the components of compositions and methods described herein comprised by serum-free (or alternatively, low serum concentration) media formulation, higher than atmospheric oxygen concentration, or both. In this experimental configuration hepatocytes are cultured alone or co-cultured with non-parenchymal cells, in the presence or absence of serum. Two seeding conditions were evaluated: one was normal atmospheric condition and the second was 95% oxygen, both under 5% $CO_2$ as is common practice. Following overnight seeding, the cultures were washed and the level of demonstrated cellular functionality at first day of culture, as exemplified by CYP1A1/2 activity, was measured by the ethoxyresorufin-O-deethylase (EROD) assay under normal oxygen condition. The result shows that, compared to the baseline condition of monocultured hepatocytes, each respective embodiment of compositions and methods described herein confers an improved cellular functionality at first day of culture. It should be emphasized that the data in Table 1 is not simply the attainment of a higher level of cellular function, but the attainment of that higher level very rapidly, at the first day of culture, thereby enabling the culture to be productively utilized on as many as six, nine, or twelve or more additional, earlier days than would be afforded under traditional cell culture or co-culture methods.

TABLE 1

CYP1A1/2 activity at first day of culture demonstrated by various embodiments of compositions and methods described herein

| Cell culture components comprised in various embodiments: | | | | |
| --- | --- | --- | --- | --- |
| none (hepatocyte monoculture) | co-culture | high oxygen | serum-free media | CYP1A1/2 activity (nM/min/1 × 10$^6$ cells) |
| X | | | | 0.89 ± 0.20 |
| | X | | X | 1.45 ± 0.35 |
| | | X | X | 2.44 ± 0.20 |
| | X | X | | 2.63 ± 0.13 |
| | X | X | X | 3.45 ± 0.21 |

Table 2 compares the metabolic function of hepatocytes co-cultured with non-parenchymal cells in serum free media, and under high oxygen tensions (95% $O_2$, 5% $CO_2$) at the first day of culture (Day 1), to that of freshly isolated hepatocytes cultured in suspension (Day 0). The activities of CYP1A1/2 and CYP2B1/2 are measured using the EROD, MROD, PROD and BROD assays respectively. As can be seen, the metabolic activity of hepatocytes in oxygenated co-cultures is equivalent or higher than that of hepatocytes in suspension.

TABLE 2

| | Cyp1a1/2 and Cyp2b1/2 activity (nM/min/1 × 10⁶ cells) | | | |
| --- | --- | --- | --- | --- |
| | EROD | MROD | PROD | BROD |
| Suspension (Day 0) | 2.73 ± 0.07 | 0.74 ± 0.10 | 0.24 ± 0.03 | 0.04 ± 0.08 |
| Oxygenated co-culture (Day 1) | 3.10 ± 0.40 | 0.83 ± 0.10 | 0.85 ± 0.35 | 0.23 ± 0.07 |

Figure 6:
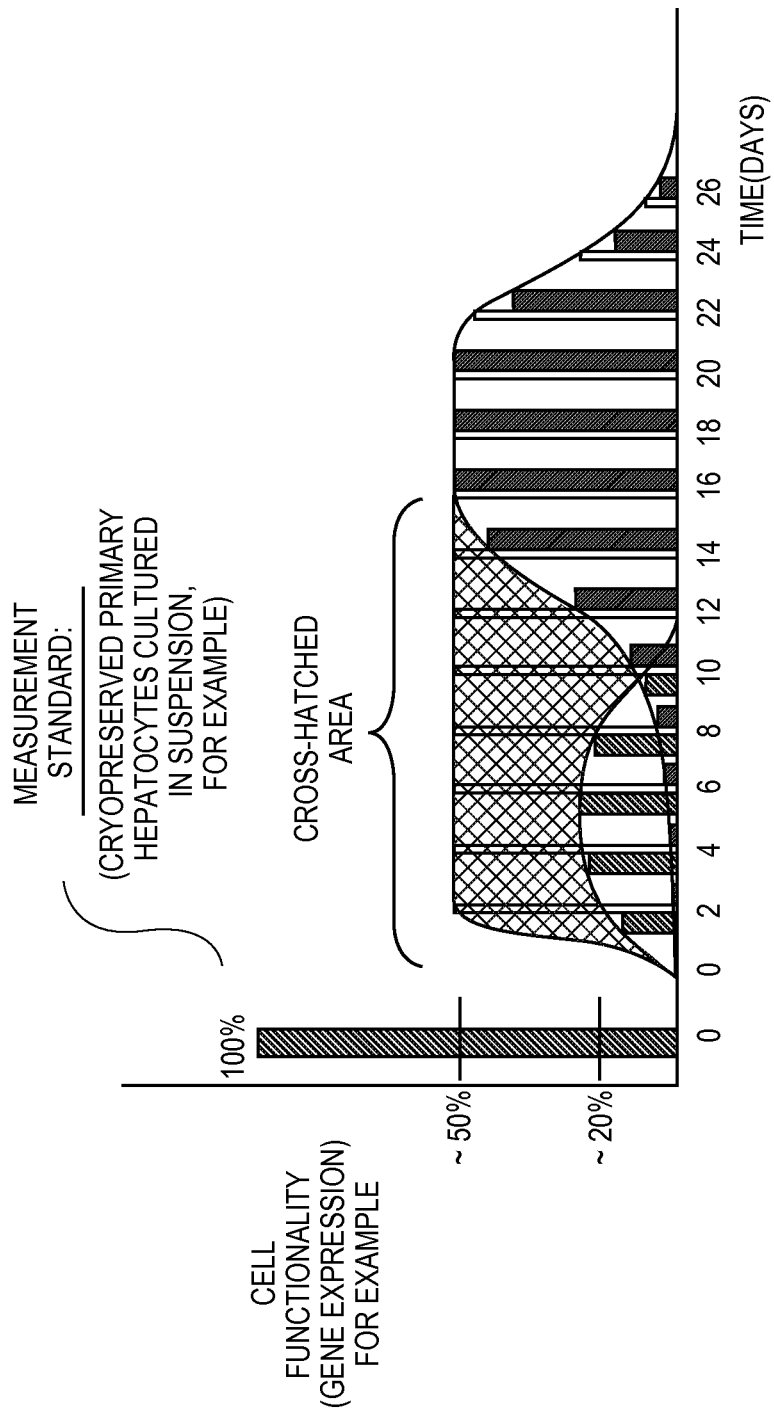
FIG. 6 is a pro forma, prophetic graphical illustration of the unexpected benefit which would be produced by an embodiment of compositions and methods described herein comprising multiple cell culture components.

FIG. 6 illustrates, on a pro forma, prophetic, conceptual basis, the time-based benefit derived from an embodiment of a cell culture system described herein, wherein the benefit area is depicted in the Figure as the cross-hatched area. In FIG. 6, the low bell curve that shows cellular functionality enduring at a low level from 0-10 days represents the performance of plated cryopreserved primary hepatocytes cultured in a mono-culture under traditional culture methods and conditions. The second bell curve that shows cellular functionality rising to a relatively higher level by Day 14 represents the performance of a traditional culture of a co-culture of plated cryopreserved primary hepatocytes with 3T3 fibroblasts. This represents co-culture without any at least a second cell culture component. The large bell curve that encompasses both the cross-hatched area and the area bounded by the second bell curve reflects the level of cellular function envisioned by at least one embodiment, including materially more rapid attainment of high functionality very close to the time of onset of the cell culture. The high cellular function beginning on the first day after culture permits use of the cell cultures more quickly than in the past; reduces tissue culture, labor, and inventory carrying costs; creates additional days of high cellular function during which the cell culture can be utilized for economically productive purposes, which days would otherwise have to be devoted to the economically unproductive, prerequisite task of additional tissue incubation and culture; and provides a more efficient system.

A Multi-Well Format Embodiment of Compositions and Methods Described Herein

A 96-well plate is coated with hydrogel. Each well is filled by serum-free media. 3T3-J2 fibroblasts are placed to each well and the plate is cultured overnight. On the following day, human hepatocytes are thawed from a cryopreserved vial and placed in 95% oxygen chamber with serum-free media. The cells are counted. To each well, discrete, pre-determined numbers of cells are seeded while maintaining high oxygen level. The 96-well plate is then culture overnight in the presence of 95% oxygen. The plate is subsequently moved to a cell culture incubator with normal oxygen level. 12 different drugs are diluted in serum free media and then added to the first row of 96-well plate. The addition is repeated in subsequent rows of 96-well plate. 5 days later, MROD assays are conducted with cell extracts obtained from each well.

In an alternative multi-well embodiment, the cell culture system is comprised in one compartment of a multi-well assay platform that is configured to comprise a culture of artificially or naturally occurring cellular material in at least one additional compartment of the platform. The several compartments of the assay platform are microfluidically interconnected by at least one microscale channel configured to conduct liquid or gaseous cell culture medium in a circulating or re-circulating pathway between and among the compartments.

In an alternative embodiment, the cell culture system is configured to comprise a cell culture compartment that is microfluidically connected to at least one microscale input or output channel, wherein the channel and the compartment are configured to conduct liquid or gaseous cell culture medium in a circulating or re-circulating pathway, and wherein the cell culture medium being configured to come into contact with the cell culture comprising compositions and methods described herein under at least one condition of perfusion or flow comprises an additional, separate and distinct component of compositions and methods described herein.

Kits

A kit is manufactured including the following components: microtiter plate, oxygen tank containing mix of gases with pre-determined ratio, an instruction manual, an instruction compact disc, frozen vials containing second cell population, and culture media, which may be low serum or serum free media. Alternatively, a kit is prepared containing a microtiter plate coated with a binding agent layer or a material to form a microscaffold and containing serum-free or low serum media. Included are vials of cryopreserved primary and secondary cells. In another embodiment, the kit comprises a chip including at least one compartment connected with microfluidic channels to permit perfusion of the culture media, oxygen containers with a mixture of gases to provide a higher than atmospheric concentration of oxygen, and a serum free culture media.

What is claimed is:

1. A cell culture system, comprising:
   a) a cell culture compartment comprising a cell culture substrate and a cell culture medium comprising no more than about 10% serum;
   b) a coculture of metabolically active primary hepatocytes and at least one other cell type, said coculture seeded onto the culture substrate and cultured in the culture medium; and
   c) a gaseous composition in contact with the culture medium and comprising at least about 90% oxygen.

2. The cell culture system of claim 1, wherein the culture medium comprises no more than about 5% serum.

3. The cell culture system of claim 1, wherein the culture medium is serum free.

4. The cell culture system of claim 1, wherein the at least one other cell type is a stromal cell type.

5. The cell culture system of claim 1, wherein the at least one other cell type is a non-parenchymal cell type.

6. The cell culture system of claim 1, wherein the ratio of the number of metabolically active primary hepatocytes to the number of cells of the at least one other cell type in the coculture is from about 1:10 to about 10:1.

7. The cell culture system of claim 1, wherein the ratio of the number of metabolically active primary hepatocytes to the number of cells of the at least one other cell type in the coculture is from about 1:5 to about 5:1.

8. The cell culture system of claim 1, wherein the gaseous composition in contact with the culture medium comprises at least about 95% oxygen.

9. The cell culture system of claim 1, wherein the gaseous composition in contact with the culture medium comprises at least about 100% oxygen.

10. The cell culture system of claim 1, wherein the coculture of metabolically active primary hepatocytes and the at least one other cell type are seeded into the culture compartment and cultured in the culture medium in contact with the gaseous composition for about one day.

11. The cell culture system of claim 10, wherein following culturing in the culture medium in contact with the gaseous composition for about one day the level of albumin secretion by hepatocytes in the coculture is at least about 4-fold higher than the level of albumin secretion by hepatocytes in a control coculture comprising a gaseous composition in contact with the culture medium and comprising an atmospheric level of oxygen.

12. The cell culture system of claim 10, wherein the level of albumin secretion by hepatocytes in the coculture is at least about 80 µg/1×10⁶ cells /24 hrs.

13. The cell culture system of claim 10, wherein the level of transcription of phase I and phase II enzymes in hepatocytes in the coculture is comparable to the level of transcription of phase I and phase II enzymes in freshly isolated hepatocytes.

14. The cell culture system of claim 10, wherein the CYP1A1/2 activity level of hepatocytes in the coculture is comparable to the CYP1A1/2 activity level in freshly isolated hepatocytes.

15. A cell culture system made by a method comprising:
 a) seeding a coculture of metabolically active primary hepatocytes and at least one other cell type onto a culture substrate; and
 b) culturing the seeded coculture in a culture medium comprising no more than about 10% serum;
 wherein during the seeding and/or culturing the culture medium is in contact with a gaseous composition comprising at least about 90% oxygen.

16. The cell culture system of claim 15, wherein the culturing is for from about one to about three days.

17. The cell culture system of claim 15, wherein the culture medium comprising no more than about 5% serum.

18. The cell culture system of claim 15, wherein the culture medium is serum free.

19. The cell culture system of claim 15, wherein the gaseous composition comprises at least about 95% oxygen.

20. The cell culture system of claim 15, wherein the gaseous composition comprises at least about 100% oxygen.

21. A cell culture system, comprising:
 a) a cell culture compartment comprising a cell culture substrate and a cell culture medium comprising no more than about 10% serum;
 b) a coculture of metabolically active primary hepatocytes and at least one other cell type, said coculture seeded onto the culture substrate and cultured in the culture medium, wherein during the seeding and/or the first one to three days of culturing the culture medium is in contact with a gaseous composition comprising at least about 90% oxygen; and
 c) a gaseous composition in contact with the culture medium and comprising at least about 90% oxygen;
 wherein the level of albumin secretion by hepatocytes in the coculture is at least about 4-fold higher than the level of albumin secretion by hepatocytes in a control coculture comprising a gaseous composition in contact with the culture medium and comprising an atmospheric level of oxygen.

22. The cell culture system of claim 21, wherein the level of albumin secretion by hepatocytes in the coculture is at least about 80 µg/1×10⁶ cells /24 hrs.

23. The cell culture system of claim 21, wherein the level of transcription of phase I and phase II enzymes in hepatocytes in the coculture is comparable to the level of transcription of phase I and phase II enzymes in freshly isolated hepatocytes.

24. The cell culture system of claim 21, wherein the CYP1A1/2 activity level of hepatocytes in the coculture is comparable to the CYP1A1/2 activity level in freshly isolated hepatocytes.

* * * * *